United States Patent
Nishimori et al.

(10) Patent No.: US 10,131,749 B2
(45) Date of Patent: Nov. 20, 2018

(54) SULFUR COMPOUND AND COMPOSITION FOR OPTICAL MATERIALS CONTAINING SAME

(71) Applicant: MITSUBISHI GAS CHEMICAL COMPANY, INC., Tokyo (JP)

(72) Inventors: Yoshihiko Nishimori, Tokyo (JP); Teruo Kamura, Tokyo (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/542,287

(22) PCT Filed: Mar. 1, 2016

(86) PCT No.: PCT/JP2016/056150
§ 371 (c)(1),
(2) Date: Jul. 7, 2017

(87) PCT Pub. No.: WO2016/152400
PCT Pub. Date: Sep. 29, 2016

(65) Prior Publication Data
US 2018/0265637 A1    Sep. 20, 2018

(30) Foreign Application Priority Data

Mar. 24, 2015 (JP) .................. 2015-060824

(51) Int. Cl.
*G02B 1/04* (2006.01)
*C08G 75/08* (2006.01)
*C07D 409/12* (2006.01)
*C07D 331/02* (2006.01)

(52) U.S. Cl.
CPC ........... *C08G 75/08* (2013.01); *C07D 331/02* (2013.01); *G02B 1/041* (2013.01)

(58) Field of Classification Search
CPC .......... C08G 75/06; C08L 41/00; G02B 1/041
See application file for complete search history.

(56) References Cited

U.S. PATENT DOCUMENTS

| | | | |
|---|---|---|---|
| 6,117,923 A | 9/2000 | Amagai et al. | |
| 6,472,495 B1 | 10/2002 | Yoshimura et al. | |
| 2003/0171533 A1 | 9/2003 | Tamura et al. | |
| 2003/0195270 A1 | 10/2003 | Ishii et al. | |
| 2004/0122201 A1 | 6/2004 | Yoshimura et al. | |
| 2005/0154073 A1 | 7/2005 | Ishii et al. | |
| 2005/0261467 A1 | 11/2005 | Tamura et al. | |
| 2010/0331515 A1 | 12/2010 | Takeuchi et al. | |
| 2014/0371475 A1 | 12/2014 | Aoki et al. | |
| 2015/0259477 A1* | 9/2015 | Kariyazono ........... | C08G 75/08 528/378 |

FOREIGN PATENT DOCUMENTS

| | | |
|---|---|---|
| CN | 101630210 | 1/2010 |
| JP | 09-110979 | 4/1997 |
| JP | 10-298287 | 11/1998 |
| JP | 2000-327677 | 11/2000 |
| JP | 2001-002783 | 1/2001 |
| JP | 2001-131257 | 5/2001 |
| JP | 2002-122701 | 4/2002 |
| JP | 2003-226718 | 8/2003 |
| JP | 2004-27203 | 1/2004 |
| JP | 2005-272418 | 10/2005 |
| KR | 10-2009-0088240 | 8/2009 |
| WO | 02/083763 | 10/2002 |
| WO | 2009/101867 | 8/2009 |
| WO | 2013/157490 | 10/2013 |
| WO | 2014/142138 | 9/2014 |

OTHER PUBLICATIONS

International Search Report issued in WIPO Patent Application No. PCT/JP2016/056150, dated May 31, 2016.

* cited by examiner

*Primary Examiner* — Christopher M Rodd
(74) *Attorney, Agent, or Firm* — Greenblum & Bernstein, P.L.C.

(57) ABSTRACT

According to one preferred embodiment of the present invention, a composition for optical materials, which contains a compound represented by formula (1) and a compound represented by formula (2), is able to be provided. This composition for optical materials enables stable storage of a compound represented by formula (2) at low cost, and also enables stable storage thereof with respect to temperature change. In addition, this composition for optical materials enables the achievement of an optical material which has good light resistance.

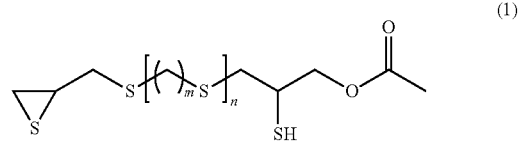

(In formula (1), m represents an integer of 0-4; and n represents an integer of 0-2.)

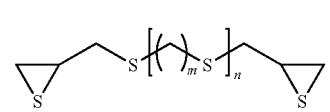

(In formula (2), m represents an integer of 0-4; and n represents an integer of 0-2.)

12 Claims, No Drawings

SULFUR COMPOUND AND COMPOSITION FOR OPTICAL MATERIALS CONTAINING SAME

TECHNICAL FIELD

The present invention relates to a novel sulfur compound and a composition for optical materials containing the same, and relates to a novel sulfur compound, which is suitably used for an optical material for a plastic lens, a prism, an optical fiber, an information recording substrate, a filter or the like, in particular for a plastic lens, and a composition for optical materials containing the same.

BACKGROUND ART

Plastic lenses are lightweight, highly tough and easy to be dyed. Properties particularly required for plastic lenses are: low specific gravity; high transparency; low yellowness; high refractive index and high Abbe number as optical properties; high heat resistance; high strength; and the like. A high refractive index allows a lens to be thinner, and a high Abbe number reduces the chromatic aberration of a lens.

Recently, many examples using an organic compound having a sulfur atom for providing a high refractive index and a high Abbe number have been reported. Among such examples, polyepisulfide compounds having a sulfur atom are known to provide a good balance between the refractive index and the Abbe number (Patent Document 1). Further, since polyepisulfide compounds can be reacted with various compounds, for the purpose of the improvement of physical properties, compositions in combination with various compounds have been proposed (Patent Documents 2-5).

However, it is difficult to store an episulfide compound for a long period of time because of its high reactivity. In this regard, techniques of keeping in cold storage (Patent Document 6) and techniques of adding an epoxy compound having a halogen group (Patent Document 7) have been proposed.

PRIOR ART DOCUMENTS

Patent Documents

Patent Document 1: Japanese Laid-Open Patent Publication No. H09-110979
Patent Document 2: Japanese Laid-Open Patent Publication No. H10-298287
Patent Document 3: Japanese Laid-Open Patent Publication No. 2001-002783
Patent Document 4: Japanese Laid-Open Patent Publication No. 2001-131257
Patent Document 5: Japanese Laid-Open Patent Publication No. 2002-122701
Patent Document 6: Japanese Laid-Open Patent Publication No. 2000-327677
Patent Document 7: Japanese Laid-Open Patent Publication No. 2005-272418

SUMMARY OF THE INVENTION

Problems to be Solved by the Invention

However, for keeping in cold storage, a dedicated cooling chamber is required and it requires much cost, and an epoxy compound having a halogen group causes deterioration of light resistance derived from halogen. For these reasons, the improvement is desired. Moreover, stable storage with respect to temperature change is desired.

In view of the above-described conventional problems, the problem to be solved by the present invention is to provide a composition for optical materials, which can stably store a polymerizable compound such as an episulfide compound at low cost and with respect to temperature change, and by which an optical material having good light resistance can be obtained.

Means for Solving the Problems

Under such circumstances, the present inventors diligently made researches and found that the above-described problems can be solved by the present invention described below. Specifically, the present invention is as follows:

<1> An episulfide compound represented by formula (1):

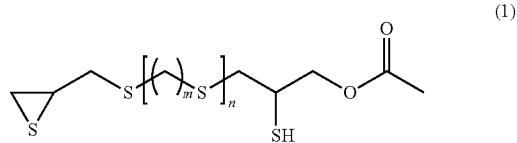

(1)

wherein m represents an integer of 0 to 4 and n represents an integer of 0 to 2.

<2> A composition for optical materials, which contains the episulfide compound according to item <1> and a polymerizable compound other than the compound.

<3> The composition for optical materials according to item <2>, wherein the content of the episulfide compound is 0.001 to 5.0% by mass.

<4> The composition for optical materials according to item <2> or <3>, wherein the content of the polymerizable compound is 95.0 to 99.999% by mass.

<5> The composition for optical materials according to any one of items <2> to <4>, which contains a compound represented by formula (2) as the polymerizable compound:

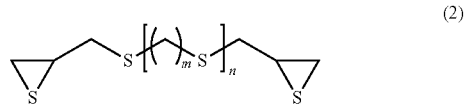

(2)

wherein m represents an integer of 0 to 4 and n represents an integer of 0 to 2.

<6> The composition for optical materials according to item <5>, wherein the content of the compound represented by formula (2) is 40 to 99.999% by mass.

<7> A polymerizable and curable composition, which contains the composition for optical materials according to any one of items <2> to <6> and a polymerization catalyst in an amount of 0.0001 to 10% by mass relative to the total amount of the composition for optical materials.

<8> An optical material obtained by curing the composition for optical materials according to any one of items <2> to <6> or the polymerizable and curable composition according to item <7>.

<9> An optical lens comprising the optical material according to item <8>.

<10> A method for producing an optical material, which comprises a step of adding a polymerization catalyst in an amount of 0.0001 to 10% by mass relative to the total amount of the composition for optical materials according to any one of items <2> to <6> to be polymerized and cured.

Advantageous Effect of the Invention

When producing an optical material having a high refractive index, according to the present invention, it is possible to produce a composition for optical materials, which can stably store a polymerizable compound such as an episulfide compound at low cost and with respect to temperature change, and by which an optical material having good light resistance can be obtained.

EMBODIMENTS FOR CARRYING OUT THE INVENTION

Hereinafter, the present invention will be described in detail.

The present invention relates to a compound represented by formula (1) above and a composition for optical materials which contains the compound represented by formula (1) and a polymerizable compound other than the compound represented by formula (1). Examples of the polymerizable compound other than the compound represented by formula (1) include an episulfide compound, a vinyl compound, a methacrylic compound, an acrylic compound and an allyl compound. Among them, an episulfide compound is preferred, and a compound represented by formula (2) above is more preferred.

The ratio of the compound represented by formula (1) in the composition for optical materials of the present invention is preferably 0.001 to 5.0% by mass, more preferably 0.005 to 3.0% by mass, and particularly preferably 0.01 to 1.0% by mass. When the ratio of the compound represented by formula (1) is less than 0.001% by mass, sufficient effects may not be obtained. When the ratio is more than 5.0% by mass, heat resistance may be reduced.

Further, the ratio of the polymerizable compound in the composition for optical materials of the present invention is preferably 95.0 to 99.999% by mass, more preferably 97.0 to 99.995% by mass, and particularly preferably 99.0 to 99.99% by mass. When using the compound represented by formula (2) above as the polymerizable compound, the ratio of the compound represented by formula (2) in the composition for optical materials is preferably 40 to 99.999% by mass, more preferably 50 to 99.995% by mass, and particularly preferably 60 to 99.99% by mass.

Hereinafter, the compound represented by formula (1) above and the compound represented by formula (2) above will be described in detail.

The present invention relates to the compound represented by formula (1) above, and the compound represented by formula (1) is used in the composition for optical materials of the present invention. In formula (1), it is preferred that m is an integer of 0 to 2 and that n is an integer of 0 or 1. More preferred is a compound in which m is 0 and n is 1 or a compound in which n is 0, and most preferred is a compound in which n is 0. As the compound represented by formula (1), such compounds may be used solely, or two or more of them may be used in combination.

Hereinafter, the method for producing the compound represented by formula (1) of the present invention will be described, but the production method is not limited thereto.

As the method for producing the compound represented by formula (1) of the present invention, the compound represented by formula (2) obtained by a publicly-known technique is reacted with acetic acid, thereby obtaining the compound represented by formula (1). Hereinafter, the method for producing the compound represented by formula (1) from the compound represented by formula (2) will be described.

The compound represented by formula (2) is reacted with acetic acid or acetic anhydride, thereby obtaining the compound represented by formula (1). Acetic acid is preferred. Acetic acid or acetic anhydride is used in the same mole number as that of the compound represented by formula (2), i.e., a theoretical amount, but when importance is placed on the reaction rate and the purity, it is used in the theoretical amount to 20 times the theoretical amount (mol). The amount is preferably from 1.5 times the theoretical amount (mol) to 10 times the theoretical amount (mol), and more preferably from twice the theoretical amount (mol) to 10 times the theoretical amount (mol). Further, a solvent is preferably used. The solvent is not particularly limited as long as it dissolves acetic acid or acetic anhydride, the compound represented by formula (1) and the compound represented by formula (2). Specific examples thereof include: ethers such as diethyl ether and tetrahydrofuran; hydroxy ethers such as methyl cellosolve, ethyl cellosolve and butyl cellosolve; aromatic hydrocarbons such as benzene and toluene; and halogenated hydrocarbons such as dichloromethane, chloroform and chlorobenzene. Preferred are ethers, aromatic hydrocarbons and halogenated hydrocarbons, and more preferred are aromatic hydrocarbons and halogenated hydrocarbons. These solvents may be used solely, or two or more of them may be used in combination.

The reaction temperature is not particularly limited as long as the reaction proceeds, but the reaction is usually performed at 10° C. to 50° C. When the reaction temperature is lower than 10° C., the reaction rate is reduced and the reaction does not proceed sufficiently, and when the temperature is higher than 50° C., polymer formation becomes pronounced.

The reaction time is not particularly limited as long as the reaction proceeds, but the reaction time is usually 10 minutes to 50 hours, preferably 30 minutes to 30 hours, and more preferably 30 minutes to 20 hours. When the reaction time is less than 10 minutes, the reaction does not proceed sufficiently, and when the reaction time is more than 50 hours, polymer formation becomes pronounced.

The reaction pressure is not particularly limited as long as the reaction proceeds and may be either elevated pressure or reduced pressure, but the reaction is usually performed under ordinary pressure.

In the composition for optical materials of the present invention, it is possible to preferably use a compound represented by formula (2) above as a polymerizable compound. Specific examples of the compound represented by formula (2) include episulfides such as bis($\beta$-epithiopropyl)sulfide, bis($\beta$-epithiopropyl)disulfide, bis($\beta$-epithiopropylthio)methane, 1,2-bis($\beta$-epithiopropylthio)ethane, 1,3-bis($\beta$-epithiopropylthio)propane and 1,4-bis($\beta$-epithiopropylthio)butane. As the compound represented by formula (2), such compounds may be used solely, or two or more compounds may be used in combination.

Among the above-described compounds, bis($\beta$-epithiopropyl)sulfide (n=0 in formula (2)) and bis($\beta$-epithiopropyl)disulfide (m=0 and n=1 in formula (2)) are preferred, and bis($\beta$-epithiopropyl)sulfide (n=0 in formula (2)) is most preferred.

The composition for optical materials of the present invention may include a polythiol compound as a polymerizable compound for improving the color tone of obtained resin at the time of heating. The content of the polythiol compound is usually 1 to 25% by mass, preferably 2 to 25% by mass, and particularly preferably 5 to 20% by mass when the total amount of the composition for optical materials is 100% by mass. When the content of the polythiol compound is less than 1% by mass, yellowing may occur at the time of lens molding, and when the content is more than 25% by mass, the heat resistance may be reduced. As the polythiol compound to be used in the present invention, compounds may be used solely, or two or more of them may be used in combination.

Specific examples thereof include methanedithiol, methanetrithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethylthio)ethane, 2,3-dimercapto-1-propanol, 1,3-dimercapto-2-propanol, 1,2,3-trimercaptopropane, 2-mercaptomethyl-1,3-dimercaptopropane, 2-mercaptomethyl-1,4-dimercaptobutane, 2-(2-mercaptoethylthio)-1,3-dimercaptopropane, 4-mercaptomethyl-1,8-dimercapto-3,6-dithiaoctane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethyleneglycol bis(2-mercaptoacetate), ethyleneglycol bis(3-mercaptopropionate), diethyleneglycol bis(2-mercaptoacetate), diethyleneglycol bis(3-mercaptopropionate), 1,4-butanediol bis(2-mercaptoacetate), 1,4-butanediol bis(3-mercaptopropionate), trimethylolpropane tris(thioglycolate), trimethylolpropane tris(mercaptopropionate), pentaerythritol tetrakis-thioglycolate, pentaerythritol tetrakis-mercaptopropionate, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethylthiomethyl)-1,4-dithiane, 2,5-dimercaptomethyl-1-thiane, 2,5-dimercaptoethyl-1-thiane, 2,5-dimercaptomethylthiophene, 1,2-dimercaptobenzene, 1,3-dimercaptobenzene, 1,4-dimercaptobenzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, 2,2-bis(4-mercaptophenyl)propane, bis(4-mercaptophenyl)ether, bis(4-mercaptophenyl)sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 2,5-dimercapto-1,3,4-thiadiazole, 3,4-thiophenedithiol and 1,1,3,3-tetrakis(mercaptomethylthio)propane.

Among them, bis(2-mercaptoethyl)sulfide, 2,5-dimercaptomethyl-1,4-dithiane, 1,3-bis(mercaptomethyl)benzene, 1,4-bis(mercaptomethyl)benzene, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, pentaerythritol tetrakis-mercaptopropionate, pentaerythritol tetrakis-thioglycolate, trimethylolpropane tris(thioglycolate) and trimethylolpropane tris(mercapto propionate) are preferred, bis(2-mercaptoethyl)sulfide, 2,5-bis(2-mercaptomethyl)-1,4-dithiane, 4-mercaptomethyl-1,8-dimercapto-3,6-dithiaoctane, 1,3-bis(mercaptomethyl)benzene, pentaerythritol tetrakis-mercaptopropionate and pentaerythritol tetrakis-thioglycolate are more preferred, and bis(2-mercaptoethyl)sulfide, 2,5-dimercaptomethyl-1,4-dithiane and 4-mercaptomethyl-1,8-dimercapto-3,6-dithiaoctane are particularly preferred.

The composition for optical materials of the present invention may include a polyisocyanate compound as a polymerizable compound for improving the strength of obtained resin. The content of the polyisocyanate compound is usually 1 to 25% by mass, preferably 2 to 25% by mass, and particularly preferably 5 to 20% by mass when the total amount of the composition for optical materials is 100% by mass. When the content of the polyisocyanate compound is less than 1% by mass, the strength may be reduced, and when the content is more than 25% by mass, the color tone may be reduced. As the polyisocyanate compound to be used in the present invention, compounds may be used solely, or two or more of them may be used in combination.

Specific examples thereof include diethylene diisocyanate, tetramethylene diisocyanate, hexamethylene diisocyanate, trimethylhexamethylene diisocyanate, cyclohexane diisocyanate, 1,3-bis(isocyanatemethyl)cyclohexane, 1,4-bis(isocyanatemethyl)cyclohexane, isophorone diisocyanate, 2,6-bis(isocyanatemethyl)decahydronaphthalene, lysine triisocyanate, tolylene diisocyanate, o-tolidine diisocyanate, diphenylmethane diisocyanate, diphenylether diisocyanate, 3-(2'-isocyanatecyclohexyl)propylisocyanate, isopropylidene bis(cyclohexyl isocyanate), 2,2'-bis(4-isocyanatephenyl)propane, triphenylmethane triisocyanate, bis(diisocyanatetolyl)phenylmethane, 4,4',4"-triisocyanate-2,5-dimethoxyphenylamine, 3,3'-dimethoxybenzidine-4,4'-diisocyanate, 1,3-phenylene diisocyanate, 1,4-phenylene diisocyanate, 4,4'-diisocyanatebiphenyl, 4,4'-diisocyanate-3,3'-dimethylbiphenyl, dicyclohexylmethane-4,4'-diisocyanate, 1,1'-methylenebis(4-isocyanatebenzene), 1,1'-methylenebis(3-methyl-4-isocyanatebenzene), m-xylylene diisocyanate, ε-xylylene diisocyanate, m-tetramethyl xylylene diisocyanate, p-tetramethyl xylylene diisocyanate, 1,3-bis(2-isocyanate-2-propyl)benzene, 2,6-bis(isocyanatemethyl)naphthalene, 1,5-naphthalene diisocyanate, bis(isocyanatemethyl)tetrahydrodicyclopentadiene, bis(isocyanatemethyl)dicyclopentadiene, bis(isocyanatemethyl)tetrahydrothiophene, bis(isocyanatemethyl)norbornene, bis(isocyanatemethyl)adamantane, thiodiethyl diisocyanate, thiodipropyl diisocyanate, thiodihexyl diisocyanate, bis[(4-isocyanatemethyl)phenyl]sulfide, 2,5-diisocyanate-1,4-dithiane, 2,5-diisocyanatemethyl-1,4-dithiane, 2,5-diisocyanatemethylthiophene, dithiodiethyl diisocyanate and dithiodipropyl diisocyanate.

However, the polyisocyanate compound which can be used in the present invention is not limited thereto, and these substances may be used solely, or two or more of them may be used in combination.

Among them, isophorone diisocyanate, tolylene diisocyanate, diphenylmethane diisocyanate, hexamethylene diisocyanate, m-xylylene diisocyanate, p-xylylene diisocyanate, m-tetramethyl xylylene diisocyanate, p-tetramethyl xylylene diisocyanate, 1,3-bis(isocyanatemethyl)cyclohexane, 1,4-bis(isocyanatemethyl)cyclohexane, bis(isocyanatemethyl)norbornene and 2,5-diisocyanatemethyl-1,4-dithiane are preferred. More preferred are isophorone diisocyanate, tolylene diisocyanate, diphenylmethane diisocyanate, hexamethylene diisocyanate, 1,3-bis(isocyanatemethyl)cyclohexane and m-xylylene diisocyanate, and particularly preferred are isophorone diisocyanate, m-xylylene diisocyanate and 1,3-bis(isocyanatemethyl)cyclohexane.

Further, the ratio of the SH groups in the polythiol compound to the NCO groups in the polyisocyanate compound, i.e., [the number of the SH groups in the polythiol compound/the number of the NCO groups in the polyisocyanate compound](SH group/NCO group) is preferably 1.0 to 2.5, more preferably 1.25 to 2.25, and particularly preferably 1.5 to 2.0. When the above-described ratio is less than 1.0, yellowing may occur at the time of lens molding, and when the ratio is more than 2.5, the heat resistance may be reduced.

The composition for optical materials of the present invention may include sulfur as a polymerizable compound for improving the refractive index of obtained resin. The content of sulfur is usually 0.1 to 15% by mass, preferably 0.2 to 10% by mass, and particularly preferably 0.3 to 5% by mass when the total amount of the composition for optical materials is 100% by mass.

The sulfur to be used in the present invention may be in any form. Specifically, the sulfur is finely-powdered sulfur, colloidal sulfur, precipitated sulfur, crystalline sulfur, sublimed sulfur or the like, and is preferably finely-powdered sulfur having fine particles.

The sulfur to be used in the present invention may be produced by any production method. Examples of methods for producing sulfur include methods of sublimation and purification from natural sulfur ores, methods of mining underground sulfur by means of the melting method, and methods of recovery using, for example, hydrogen sulfide obtained in the process of desulfurization of petroleum oil, natural gas or the like, as a raw material, but any of these production methods may be employed.

It is preferred that the particle size of the sulfur to be used in the present invention is less than 10 mesh, that is, the sulfur is in the form of fine powder having a particle size of less than 10 mesh. When the particle size of the sulfur is more than 10 mesh, it is difficult to dissolve the sulfur completely. For this reason, an undesirable reaction or the like may be caused in the first step to generate a defect. The particle size of the sulfur is more preferably less than 30 mesh, and most preferably less than 60 mesh.

The purity of the sulfur to be used in the present invention is preferably at least 98%, more preferably at least 99.0%, even more preferably at least 99.5%, and most preferably at least 99.9%. When the purity of the sulfur is at least 98%, the color tone of the obtained optical material is improved compared to the case of lower than 98%.

When obtaining an optical material by polymerizing and curing the composition for optical materials of the present invention, it is preferred to add a polymerization catalyst. The composition of the present invention may be a polymerizable and curable composition containing a composition for optical materials and a polymerization catalyst. As the polymerization catalyst, amines, phosphines or onium salts may be used, but onium salts are particularly preferred. Among them, quaternary ammonium salts, quaternary phosphonium salts, tertiary sulfonium salts and secondary iodonium salts are preferred. Among them, quaternary ammonium salts and quaternary phosphonium salts, which have good compatibility with the composition for optical materials, are more preferred, and quaternary phosphonium salts are even more preferred. More preferred examples of the polymerization catalyst include quaternary ammonium salts such as tetra-n-butylammonium bromide, triethylbenzyl ammonium chloride, cetyldimethylbenzyl ammonium chloride and 1-n-dodecyl pyridinium chloride and quaternary phosphonium salts such as tetra-n-butylphosphonium bromide and tetraphenyl phosphonium bromide. Among them, tetra-n-butylammonium bromide, triethylbenzyl ammonium chloride and tetra-n-butylphosphonium bromide are even more preferred polymerization catalysts.

The amount of the polymerization catalyst to be added cannot be determined categorically because it varies depending on the components of the composition, the mixing ratio and the method for polymerization and curing, but the amount is usually 0.0001% by mass to 10% by mass, preferably 0.001% by mass to 5% by mass, more preferably 0.01% by mass to 1% by mass, and most preferably 0.01% by mass to 0.5% by mass when the total amount of the composition for optical materials is 100% by mass (amount not including the polymerization catalyst). When the amount of the polymerization catalyst to be added is more than 10% by mass, the composition may be rapidly polymerized. When the amount of the polymerization catalyst to be added is less than 0.0001% by mass, the composition for optical materials may be insufficiently cured, resulting in poor heat resistance.

Moreover, in the production of the optical material according to the production method of the present invention, it is surely possible to add additives such as an ultraviolet absorber, a blueing agent and a pigment to the composition for optical materials to further improve practicability of the optical material obtained.

Preferred examples of the ultraviolet absorber include benzotriazole-based compounds, and 2-(2-hydroxy-5-methylphenyl)-2H-benzotriazol, 5-chloro-2-(3,5-di-tert-butyl-2-hydroxyphenyl)-2H-benzotriazol, 2-(2-hydroxy-4-octylphenyl)-2H-benzotriazol, 2-(2-hydroxy-4-methoxyphenyl)-2H-benzotriazol, 2-(2-hydroxy-4-ethoxyphenyl)-2H-benzotriazol, 2-(2-hydroxy-4-butoxyphenyl)-2H-benzotriazol, 2-(2-hydroxy-4-octyloxyphenyl)-2H-benzotriazol and 2-(2-hydroxy-5-t-octylphenyl)-2H-benzotriazol are particularly preferred compounds.

The amount of each of such ultraviolet absorbers to be added is usually 0.01 to 5% by mass when the total amount of the composition for optical materials is 100% by mass.

When polymerizing and curing the composition for optical materials, for the purpose of extension of the pot life, dispersion of heat generated by polymerization, etc., a polymerization modifier may be added according to need. Examples of the polymerization modifier include halides of groups 13 to 16 of the long form of the periodic table. Among them, halides of silicon, germanium, tin and antimony are preferred, and chlorides of germanium, tin and antimony, which have an alkyl group, are more preferred. Further, dibutyltin dichloride, butyltin trichloride, dioctyltin dichloride, octyltin trichloride, dibutyldichlorogermanium, butyltrichlorogermanium, diphenyldichlorogermanium, phenyltrichlorogermanium and triphenylantimony dichloride are even more preferred, and dibutyltin dichloride is the most preferred compound. These polymerization modifiers may be used solely, or two or more of them may be used in combination.

The amount of the polymerization modifier to be added is 0.0001 to 5.0% by mass, preferably 0.0005 to 3.0% by mass, and more preferably 0.001 to 2.0% by mass when the total amount of the composition for optical materials is 100% by mass. When the amount of the polymerization modifier to be added is less than 0.0001% by mass, sufficient pot life cannot be ensured in the obtained optical material, and when the amount of the polymerization modifier to be added is more than 5.0% by mass, the composition for optical materials may not be sufficiently cured, and the heat resistance of the obtained optical material may be reduced.

The composition for optical materials or polymerizable and curable composition thus obtained is injected into a mold or the like and polymerized to obtain an optical material.

At the time of cast-molding the composition of the present invention, it is preferred to filter and remove impurities using, for example, a filter having a pore diameter of about 0.1 to 5 μm in terms of improving the quality of the optical material of the present invention.

The composition of the present invention is usually polymerized as described below. Specifically, the curing time is usually 1 to 100 hours, and the curing temperature is usually −10° C. to 140° C. The polymerization is conducted by carrying out a step of retaining the composition at a predetermined polymerization temperature for a predetermined amount of time, a step of increasing the temperature at a rate of 0.1° C. to 100° C./h and a step of decreasing the temperature at a rate of 0.1° ° C. to 100° C./h, or a combination of these steps.

Further, it is preferred to anneal the obtained optical material at a temperature of 50 to 150° C. for about 10 minutes to 5 hours after curing is completed in terms of eliminating distortion of the optical material of the present invention. Moreover, the obtained optical material may be subjected to a surface treatment such as dyeing, hard coating, impact-resistant coating, antireflection treatment and imparting antifog properties according to need.

The optical material of the present invention can be suitably used as an optical lens. An optical lens produced by using the composition of the present invention is excellent in stability, color phase, light resistance and transparency, and therefore can be used in the field in which expensive glass lenses having a high refractive index have been conventionally used including telescopes, binoculars and television projectors and is very useful. The optical lens is preferably used in the form of an aspherical lens according to need. In the case of the aspherical lens, since the spherical aberration can be adjusted to be substantially zero by one lens, it is not necessary to remove the spherical aberration by combining a plurality of spherical lenses, and reduction in weight and reduction in the production cost can be carried out. Accordingly, the aspherical lens is particularly useful as a camera lens among optical lenses.

EXAMPLES

Hereinafter, the present invention will be specifically described by way of working examples and comparative examples. However, the present invention is not limited to the below-described working examples.
1. Storage Stability
Change in the purity of the episulfide compound as the main component in the composition for optical materials was followed under nitrogen atmosphere at 60° C. for 1 week by GPC analysis (detection was carried out by RID-10A (Shimadzu Corporation) using a column GPC K-801 (Showa Denko K.K.)). The case where the purity reduction is less than 5% was rated as "A". The case where the purity reduction is 5% or more and less than 10% was rated as "B". The case where the purity reduction is 10% or more was rated as "C". A and B are regarded as acceptable.
2. Temperature Change Stability
The sample was stored under nitrogen atmosphere at −10° C. for 20 hours; subsequently the temperature was elevated to 30° C. over 4 hours and the sample was stored at 30° C. for 20 hours; and subsequently the temperature was lowered to −10° C. over 4 hours. This operation was repeated 10 times. After that, 40 g of special grade acetone (99.5% or more, Kanto Chemical Co., Inc.) was added to 10 g of the episulfide compound, and after sufficiently stirred, it was allowed to stand for 10 minutes. The turbidity of this solution was measured using T-2600DA manufactured by Tokyo Denshoku Co., Ltd. The case where the turbidity is less than 1.0 ppm was rated as "A". The case where the turbidity is 1.0 ppm or more and less than 3.0 ppm was rated as "B". The case where the turbidity is 3.0 ppm or more and less than 5.0 ppm was rated as "C". The case where the turbidity is 5.0 ppm or more was rated as "D". A, B and C are regarded as acceptable.
3. Evaluation of Light Resistance (Color Tone Measurement)
(1) Measurement of Initial Value
A flat plate having a thickness of 3.0 mm was prepared according to the method described in the Examples, and the YI value was measured using a colorimeter JS-555 manufactured by Color Techno System Corporation. This value is "p".
(2) Measurement of Color Tone Change Caused by Light
After the initial value was measured, it was irradiated with carbon arc burning light for 60 hours, and after that, the YI value was measured. This value is "q".
The value of (q−p)/p was calculated. The case where the value is less than 1.0 was rated as "A". The case where the value is 1.0 or more and less than 2.0 was rated as "B". The case where the value is 2.0 or more was rated as "C". A and B are regarded as acceptable.
4. Distortion
A −4D lens was prepared according to the method described in the Examples, and the distortion was evaluated using a lens meter (distortion detector SVP-10-II manufactured by Toshiba Corporation). The case where the lens does not have distortion was rated as "A". The case where the lens has distortion was rated as "B". A is regarded as acceptable.

Example 1

150 g of acetic acid was added to 100 g of bis(β-epithiopropyl)sulfide (hereinafter referred to as "the compound a") as the above-described compound represented by formula (2) and 200 ml of toluene, and the mixture was reacted at 40° C. for 10 hours. After the reaction was completed, water was added thereto to carry out washing, the obtained organic layer was further washed with water 3 times, the solvent was distilled away, and then purification was carried out in a column, thereby obtaining 12 g of a compound represented by formula below (hereinafter referred to as "the compound b") as the compound represented by formula (1).

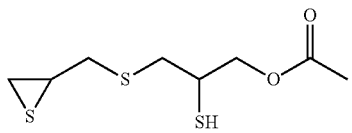

¹H-NMR (CDCl₃): 1.5 ppm (1H), 2.0 ppm (3H), 2.2 ppm (2H), 2.5 ppm (1H), 2.7-2.8 ppm (4H), 3.4 ppm (1H), 4.3 ppm (2H)
¹³C-NMR (CDCl₃): 17 ppm, 25 ppm, 33 ppm, 37 ppm (2H), 44 ppm, 74 ppm, 171 ppm Example 2

150 g of acetic acid was added to 100 g of bis(Q-epithiopropyl)disulfide (hereinafter referred to as "the compound c") as the above-described compound represented by formula (2) and 200 ml of toluene, and the mixture was reacted at 40° C. for 10 hours. After the reaction was completed, water was added thereto to carry out washing, the obtained organic layer was further washed with water 3 times, the solvent was distilled away, and then purification was carried out in a column, thereby obtaining 10 g of a compound represented by formula below (hereinafter referred to as "the compound d") as the compound represented by formula (1).

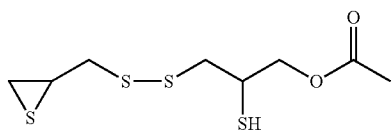

$^1$H-NMR (CDCl$_3$): 1.5 ppm (1H), 2.0 ppm (3H), 2.2 ppm (2H), 2.5 ppm (1H), 2.8-3.0 ppm (4H), 3.4 ppm (1H), 4.3 ppm (2H) $^{13}$C-NMR (CDCl$_3$): 17 ppm, 24 ppm, 32 ppm, 35 ppm, 40 ppm, 46 ppm, 74 ppm, 171 ppm Examples 3-9

To the compound a (compound of formula (2)), the compound b (compound of formula (1)) was added in an amount shown in Table 1 to evaluate storage stability and temperature change stability. The results are shown in Table 1.

Examples 10-16

To the compound c (compound of formula (2)), the compound d (compound of formula (1)) was added in an amount shown in Table 1 to evaluate storage stability and temperature change stability. The results are shown in Table 1.

Comparative Example 1

The stability of only the compound a (compound of formula (2)) was evaluated. The results are shown in Table 1.

Comparative Example 2

The stability of only the compound c (compound of formula (2)) was evaluated. The results are shown in Table 1.

TABLE 1

| Examples | Main component | Added component and amount thereof (% by mass) | Storage stability | Temperature change stability |
|---|---|---|---|---|
| Example 3 | Compound a | Compound b 0.001 | B | C |
| Example 4 | Compound a | Compound b 0.005 | B | B |
| Example 5 | Compound a | Compound b 0.01 | A | A |
| Example 6 | Compound a | Compound b 1.0 | A | A |
| Example 7 | Compound a | Compound b 3.0 | A | B |
| Example 8 | Compound a | Compound b 5.0 | A | C |
| Example 9 | Compound a | Compound b 7.0 | A | D |
| Comparative Example 1 | Compound a | None | C | D |
| Example 10 | Compound c | Compound d 0.001 | B | C |
| Example 11 | Compound c | Compound d 0.005 | B | B |

TABLE 1-continued

| Examples | Main component | Added component and amount thereof (% by mass) | Storage stability | Temperature change stability |
|---|---|---|---|---|
| Example 12 | Compound c | Compound d 0.01 | A | A |
| Example 13 | Compound c | Compound d 1.0 | A | A |
| Example 14 | Compound c | Compound d 3.0 | A | B |
| Example 15 | Compound c | Compound d 5.0 | A | C |
| Example 16 | Compound c | Compound d 7.0 | A | D |
| Comparative Example 2 | Compound c | None | C | D |

According to the results in Table 1, it is understood that excellent storage stability is obtained by adding the compound represented by formula (1) (compound b or d) to the compound represented by formula (2) (compound a or c).

Examples 17-23

With the compound a (compound of formula (2)), the compound b (compound of formula (1)) was mixed in an amount shown in Table 2 to obtain a composition for optical materials, to which 2-(2-hydroxy-5-t-octylphenyl)-2H-benzotriazol as an ultraviolet absorber was added in an amount of 1.0% by mass, and tetra-n-butylphosphonium bromide as a polymerization catalyst was added in an amount of 0.05% by mass, respectively relative to the total amount of the composition for optical materials. After that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was retained at 30° C. for 10 hours, then the temperature was elevated to 100° C. over 10 hours at a constant rate, and finally, it was retained at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The light resistance of the flat plate was evaluated (color tone measurement), and the results thereof are shown in Table 2 together with the results regarding distortion of the −4D lens.

Comparative Example 3

To the compound a (compound of formula (2)), 2-(2-hydroxy-5-t-octylphenyl)-2H-benzotriazol as an ultraviolet absorber was added in an amount of 1.0% by mass, and tetra-n-butylphosphonium bromide as a polymerization catalyst was added in an amount of 0.05% by mass, and after that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was retained at 30° C. for 10 hours, then the temperature was elevated to 100° C. over 10 hours at a constant rate, and finally, it was retained at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The light resistance of the flat plate was evaluated (color tone measurement), and the results thereof are shown in Table 2 together with the results regarding distortion of the −4D lens.

Examples 24-30

With the compound c (compound of formula (2)), the compound d (compound of formula (1)) was mixed in an amount shown in Table 2 to obtain a composition for optical materials, to which 2-(2-hydroxy-5-t-octylphenyl)-2H-benzotriazol as an ultraviolet absorber was added in an amount of 1.0% by mass, and N,N-dimethylcyclohexylamine as a polymerization catalyst was added in an amount of 0.5% by mass. After that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was retained at 30° C. for 10 hours, then the temperature was elevated to 100° C. over 10 hours at a constant rate, and finally, it was retained at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The light resistance of the flat plate was evaluated (color tone measurement), and the results thereof are shown in Table 2 together with the results regarding distortion of the −4D lens.

Comparative Example 4

To the compound c (compound of formula (2)), 2-(2-hydroxy-5-t-octylphenyl)-2H-benzotriazol as an ultraviolet absorber was added in an amount of 1.0% by mass, and N,N-dimethylcyclohexylamine as a polymerization catalyst was added in an amount of 0.5% by mass, and after that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was retained at 30° C. for 10 hours, then the temperature was elevated to 100° C. over 10 hours at a constant rate, and finally, it was retained at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The light resistance of the flat plate was evaluated (color tone measurement), and the results thereof are shown in Table 2 together with the results regarding distortion of the −4D lens.

TABLE 2

| Examples | Main component | Added component and amount thereof (% by mass) | Light resistance | Distortion |
|---|---|---|---|---|
| Example 17 | Compound a | Compound b 0.001 | B | A |
| Example 18 | Compound a | Compound b 0.005 | A | A |
| Example 19 | Compound a | Compound b 0.01 | A | A |
| Example 20 | Compound a | Compound b 1.0 | A | A |
| Example 21 | Compound a | Compound b 3.0 | A | B |
| Example 22 | Compound a | Compound b 5.0 | A | B |
| Example 23 | Compound a | Compound b 7.0 | A | B |
| Comparative Example 3 | Compound a | None | C | A |
| Example 24 | Compound c | Compound d 0.001 | B | A |
| Example 25 | Compound c | Compound d 0.005 | B | A |
| Example 26 | Compound c | Compound d 0.01 | A | A |
| Example 27 | Compound c | Compound d 1.0 | A | A |
| Example 28 | Compound c | Compound d 3.0 | A | B |
| Example 29 | Compound c | Compound d 5.0 | A | B |
| Example 30 | Compound c | Compound d 7.0 | A | B |
| Comparative Example 4 | Compound c | None | C | A |

Example 4

According to the results in Table 2, it is understood that excellent light resistance is obtained by adding the compound represented by formula (1) (compound b or d) to the compound represented by formula (2) (compound a or c).

The invention claimed is:

1. An episulfide compound represented by formula (1):

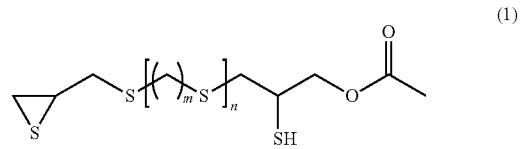

(1)

wherein m represents an integer of 0 to 4 and n represents an integer of 0 to 2.

2. A composition for optical materials, which contains the episulfide compound according to claim 1 and a polymerizable compound other than the compound.

3. The composition for optical materials according to claim 2, wherein the content of the episulfide compound is 0.001 to 5.0% by mass.

4. The composition for optical materials according to claim 2, wherein the content of the polymerizable compound is 95.0 to 99.999% by mass.

5. The composition for optical materials according to claim 2, which contains a compound represented by formula (2) as the polymerizable compound:

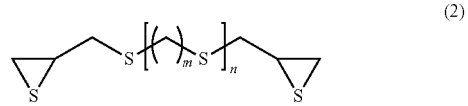

(2)

wherein m represents an integer of 0 to 4 and n represents an integer of 0 to 2.

6. The composition for optical materials according to claim 5, wherein the content of the compound represented by formula (2) is 40 to 99.999% by mass.

7. A polymerizable and curable composition, which contains the composition for optical materials according to claim 2, and a polymerization catalyst in an amount of 0.0001 to 10% by mass relative to the total amount of the composition for optical materials.

8. An optical material obtained by curing the composition for optical materials according to claim 2.

9. An optical lens comprising the optical material according to claim 8.

10. A method for producing an optical material, which comprises adding a polymerization catalyst in an amount of 0.0001 to 10% by mass relative to the total amount of the composition for optical materials according to claim 2 to be polymerized and cured.

11. An optical material obtained by curing the polymerizable and curable composition according to claim 7.

12. An optical lens comprising the optical material according to claim 11.

* * * * *